(12) United States Patent
Heller et al.

(10) Patent No.: US 9,036,396 B2
(45) Date of Patent: May 19, 2015

(54) APPARATUS AND METHOD FOR DETECTING REFLOW PROCESS

(75) Inventors: Tal Heller, Aloney Abba (IL); Sukhminder Singh Lobana, Fremont, CA (US); Yacov Duzly, Raanana (IL)

(73) Assignee: SanDisk Technologies, Inc., Plano, TX (US)

( * ) Notice: Subject to any disclaimer, the term of this patent is extended or adjusted under 35 U.S.C. 154(b) by 123 days.

(21) Appl. No.: 13/600,029

(22) Filed: Aug. 30, 2012

(65) Prior Publication Data

US 2014/0063900 A1    Mar. 6, 2014

(51) Int. Cl.
  *G11C 11/00* (2006.01)
  *G01K 7/16* (2006.01)
  *G01N 25/02* (2006.01)

(52) U.S. Cl.
  CPC *G01K 7/16* (2013.01); *G01N 25/02* (2013.01); *G11C 11/00* (2013.01)

(58) Field of Classification Search
  USPC .............................. 365/148, 163, 189.16, 211
  See application file for complete search history.

(56) References Cited

U.S. PATENT DOCUMENTS

| | | | |
|---|---|---|---|
| 6,021,046 A | 2/2000 | McLellan et al. | |
| 7,020,014 B2 * | 3/2006 | Khouri et al. | 365/163 |
| 7,859,894 B2 * | 12/2010 | Happ et al. | 365/163 |
| 7,993,963 B2 | 8/2011 | Kang et al. | |
| 8,134,866 B2 * | 3/2012 | Bae et al. | 365/163 |
| 8,179,717 B2 * | 5/2012 | Shepard et al. | 365/185.02 |
| 8,526,226 B2 * | 9/2013 | Lym et al. | 365/163 |
| 8,583,398 B2 * | 11/2013 | Cheng et al. | 702/130 |
| 2011/0007489 A1 | 1/2011 | Ohigashi et al. | |
| 2011/0075482 A1 | 3/2011 | Shepard et al. | |
| 2011/0107049 A1 | 5/2011 | Kwon et al. | |

OTHER PUBLICATIONS

Numonyx, "Phase Change Memory Technology", 2008, 19 pages.
Siliconfareast.com, "Industry-Standard Reliability Tests", 2003. http://www.siliconfareast.com/reltests.htm, 3 pages.
Kun Ren et al, Degeneration of SET-state Resistance Consistency as SI Increases in $Si_xSb_2Te_3$, Nano-Micro Letter, Jun. 2011, 4 pages.
Ron Neale, "PCM progress report No. 1: Temperatures rise and constituents on the move", EE Times-Asia, 2011, 5 pages.

* cited by examiner

*Primary Examiner* — Pho M Luu
(74) *Attorney, Agent, or Firm* — Martine Penilla Group, LLP

(57) ABSTRACT

Circuitry and method for detecting occurrence of a reflow process to an embedded storage device are disclosed. A temperature sensing device includes a resistor, a temperature sensor, and a comparator. The first terminal of the resistor is coupled to a voltage source, and the second terminal of the resistor is coupled to both the first terminal of the temperature sensor and the first input of the comparator. The second terminal of the temperature sensor is grounded and the second input of the comparator is coupled to a reference voltage. The resistance state of the temperature sensor changes from a first resistance state to a second resistance state when the temperature surrounding the temperature sensor reaches a threshold. The comparator generates an output based on the resistance changes of the temperature sensor. The generated output may indicate whether a reflow process has occurred to the embedded storage device.

20 Claims, 9 Drawing Sheets

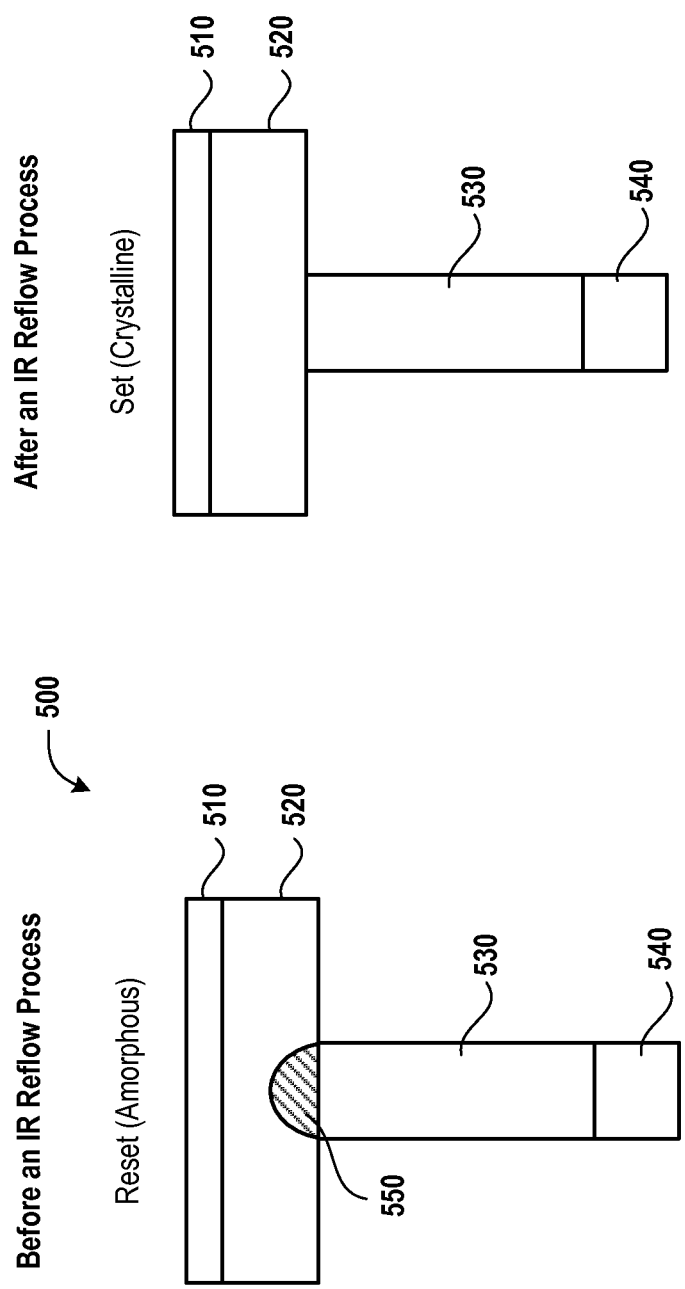

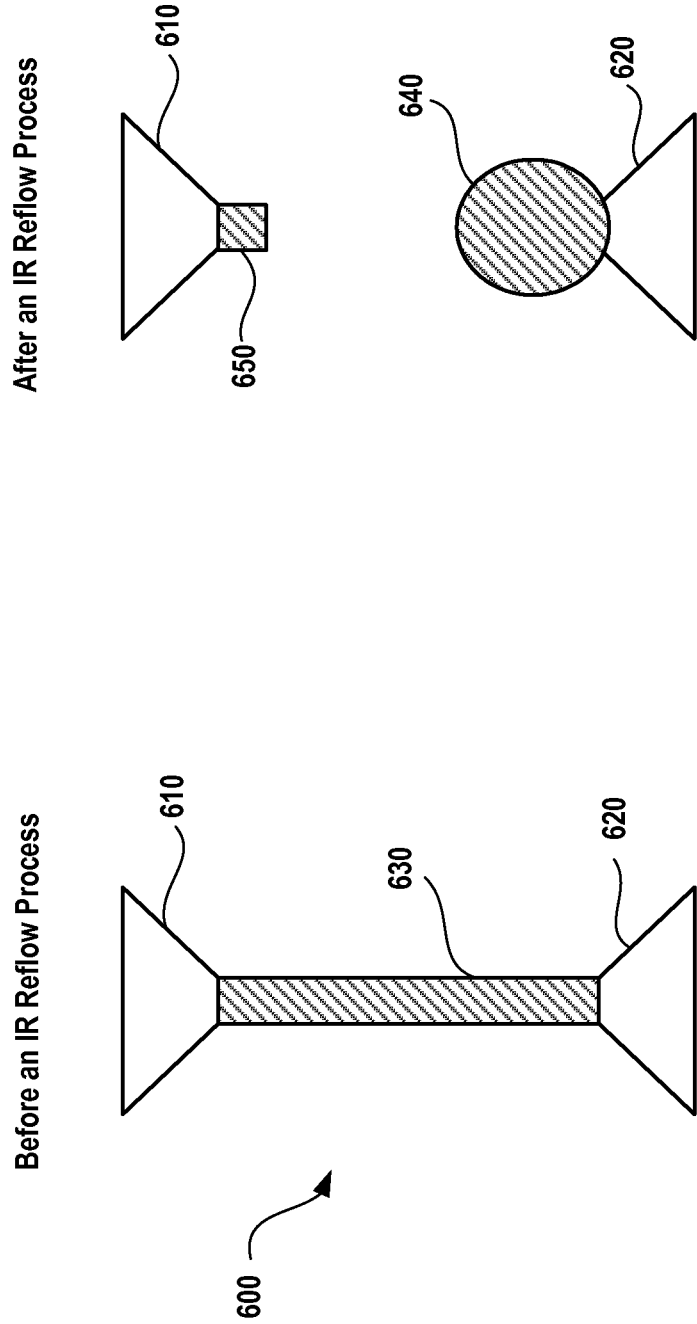

US 9,036,396 B2

APPARATUS AND METHOD FOR DETECTING REFLOW PROCESS

BACKGROUND

Reflow soldering is widely used in the semiconductor industry to attach surface mount electronic devices to a circuit board. At the beginning of a reflow process, a solder paste (a sticky mixture of powered solder and flux) is applied to areas of the circuit board that require soldering so as to temporarily attach the electronic devices, via the solder contact pads of the electronic devices, to the circuit board. Thereafter, the entire assembly is subjected to controlled heat, which melts the solder contact pads to form the solder joints that permanently connect the electronic devices to the circuit board.

The heat used to melt the solder contact pads during a reflow process can potentially cause the semiconductor chips inside the electronic devices to experience thermal shock for a short period of time. If the electronic devices are memory storage devices, the thermal shock that occurred during a reflow process could reduce data retention that creates threshold voltage shifts for the memory chips. Even worse, when the memory chips of the memory storage device are programmed with a fast programming speed, the thermal shock to memory chips may also damage the data structure of the memory chips, leading to preloaded data corruption. One way to have good resiliency to preloaded data during a reflow process is to slow down the programming speed of the memory chips in the memory storage device. However, the slow programming speed will compromise the performance of the memory storage device, especially when the memory chips in the memory storage device do not contain any preloaded data.

It is within this context that the present invention arises.

SUMMARY

Embodiments of the present disclosure provide methods and circuitry for detecting a reflow process for an embedded storage device. It should be appreciated that the present disclosure can be implemented in numerous ways, such as a process, an apparatus, a system, a device or a method on a computer readable medium. Several inventive embodiments of the present disclosure are described below.

In one embodiment, a temperature sensing device is disclosed. The temperature sensing device includes a resistor, a temperature sensor, and a comparator. The first terminal of the temperature sensor is coupled to both the first input of the comparator and the second terminal of the resistor. The first terminal of the resistor is coupled to a voltage source. The second input of the comparator is coupled to a reference voltage. The second terminal of the temperature sensor is grounded. The resistance of the temperature sensor changes from a first resistance state to a second resistance state when the temperature that surrounds the temperature sensor reaches a pre-defined threshold. The comparator may generate an output based on the resistance changes of the temperature sensor to indicate the temperature changes for the temperature sensing device. In one embodiment, the temperature sensor is a phase change memory (PCM) cell. In another embodiment, the temperature sensor is a metal device the resistance of which changes when the temperature surrounds the metal device reaches a pre-defined threshold.

In another embodiment, a system for detecting a reflow process is disclosed. The disclosed system includes a host and an embedded storage device coupled to the host. The embedded storage device includes a plurality of memory chips, a controller, and a temperature sensor. The controller is respectively coupled to the plurality of memory chips and the temperature sensor. The host is coupled to the embedded storage device via the controller of the embedded storage device. The resistance of the temperature sensor changes from a first resistance state to a second resistance state after a reflow process for the embedded storage device.

In yet another embodiment, a method for programming an embedded storage device is disclosed. The disclosed method includes generating an output by the embedded storage device based on a resistance state of a temperature sensor disposed inside the embedded storage device and determining whether a reflow process has occurred to the embedded storage device based on the generated output. If the reflow process has occurred to the embedded storage device, the memory chips of the embedded storage device are set to a fast programming mode.

Other aspects and advantages of the invention will become more apparent from the following detailed description, taken in conjunction with the accompanying drawings, illustrating by way of example the present invention.

BRIEF DESCRIPTION OF THE DRAWINGS

The disclosure may best be understood by reference to the following description taken in conjunction with the accompanying drawings.

FIGS. 5A and 5B illustrate resistance changes of a phase change memory (PCM) cell before and after an IR reflow process, in accordance with one embodiment of the present invention.

FIGS. 6A and 6B illustrate resistance changes of a metal device before and after an IR reflow process, in accordance with one embodiment of the present invention.

DETAILED DESCRIPTION

Figure 1:
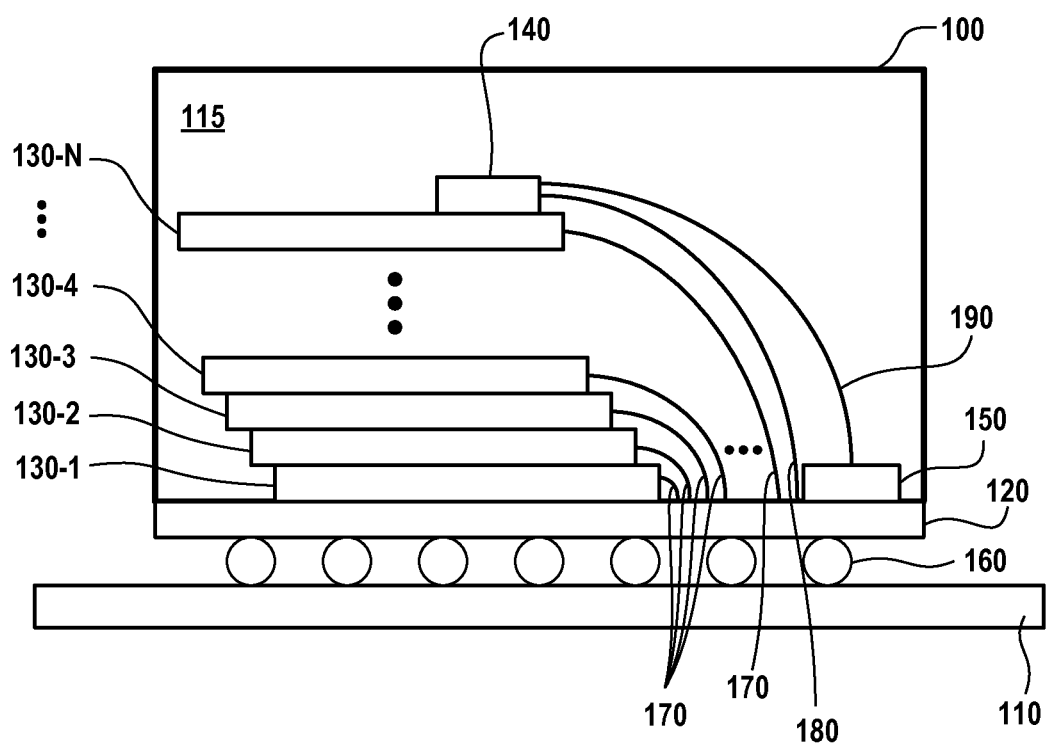
FIG. 1 illustrates an embedded storage device that is surface mounted to a substrate through a reflow process, in accordance with one embodiment of the present invention.

Embodiments defining circuitry and methods for detecting reflow processes are disclosed. For completeness, the following description sets forth numerous specific details such as examples of specific systems, components, methods, and so forth, in order to provide a good understanding of several embodiments of the present disclosure. It will be apparent to one skilled in the art, however, that at least some embodiments of the present disclosure may be practiced without these specific details. In other instances, well-known components or methods are not described in detail or are presented in a simple block diagram format in order to avoid unnecessarily obscuring the present disclosure. Thus, the specific details set forth are merely exemplary. Particular implementations may vary from these exemplary details and still be contemplated to be within the spirit and scope of the present disclosure.

Reference in the description to "one embodiment" or "an embodiment" means that a particular feature, structure, or characteristic described in connection with the embodiment is included in at least one embodiment of the disclosure. The appearances of the phrase "in one embodiment" in various places in the specification do not necessarily all refer to the same embodiment.

Although the operations of the method(s) herein are shown and described in a particular order, the order of the operations of each method may be altered so that certain operations may be performed in an inverse order or so that certain operation may be performed, at least in part, concurrently with other operations. In another embodiment, instructions or sub-operations of distinct operations may be in an intermittent and/or alternating manner.

Broadly speaking, methods and circuitry for detecting a reflow process are disclosed. In one embodiment, a temperature sensing device includes a resistor, a temperature sensor, and a comparator. A first terminal of the temperature sensor is coupled to both a first input of the comparator and a second terminal of the resistor. A first terminal of the resistor is coupled to a voltage source. The second input of the comparator is coupled to a reference voltage. The second terminal of the temperature sensor is grounded. The resistance of the temperature sensor changes from a first resistance state to a second resistance state when the temperature that surrounds the temperature sensor reaches a pre-defined threshold. The comparator may generate an output based on resistance changes of the temperature sensor to indicate whether a reflow process has occurred.

The temperature sensing device may be disposed inside an embedded storage device. If the output of the comparator of the temperature sensing device indicates that a reflow process has not occurred to the embedded storage device, the memory chips of the embedded storage device may be set to a slow programming mode. Otherwise, the memory chips of the embedded storage device may be set to a fast programming mode.

FIG. 1 illustrates an embedded storage device 100 that is surface mounted to a substrate 110 through a reflow process, in accordance with one embodiment of the present invention. The embedded storage device 100 includes a plurality of memory chips (130_1, 130_2, 130_3, 130_4, ... 130_N), a controller 140, a sensor device 150, and an interposer substrate 120. In this example, the plurality of memory chips are attached one next to another with the memory chip 130_1 being attached to the interpose substrate 120 and with the memory chip 130_N being on the top of the memory chip stack. The plurality of memory chips (130_1, 130_2, 130_3, 130_4, ... 130_N) are respectively connected to the interpose substrate 120 via the bonding wires 170. In one embodiment, the plurality of memory chips 130_1 to 130_N of the embedded storage device 100 is NAND flash memory chips. The memory chips 130_1 to 130_N may be pre-programmed with user data before the embedded storage device 100 is attached to the substrate 110 through a reflow process. Examples of pre-programmed user data for a memory chip include, without limitation, data, files, songs, maps, movies, video games, etc.

In one embodiment, the controller 140, disposed on the top of the memory chip 130_N, is respectively connected to the interpose substrate 120 via the bonding wire 180 and the sensor device 150 via the bonding wire 190. The controller 140 may be used to control the input and output of the memory chips 130_1 to 130_N, and to configure the programming speed for the memory chips 130_1 to 130_N. In one embodiment, the controller 140 may be used to generate an output that indicates whether a reflow process has occurred to the embedded storage device 100, based on the resistance change of the sensor device 150. A plastic encapsulation 115 surrounds and protects the plurality of memory chips 130_1 to 130_N, the controller 140, the sensor device 150, the bonding wires 170, 180, and 190, and the interpose substrate 120. Although this example shows a plurality of memory chips 130_1 to 130_N being connected to a controller 140, it is possible that a single chip can be encapsulated and connected to the sensor device 150.

In one embodiment, the sensor device 150 is attached to the interpose substrate 120. The sensor device 150 may be made of a phase change material the resistance of which changes from a first resistance state to a second resistance state as the temperature surrounding the sensor device 150 reaches to a pre-defined threshold. The threshold temperature is in the range of about 250° C. to 300° C.

In one embodiment, beneath the embedded storage device 100, solder balls 160 are used to surface mount the embedded storage device 100 to the substrate 110. The substrate 110 may be a printed circuit board (PCB). The solder balls 160 may be arranged in the form of a ball grid array or other arrangement. The embedded storage device 100 may be attached to the substrate 110 by an infra-red (IR) reflow process.

Figure 1A:
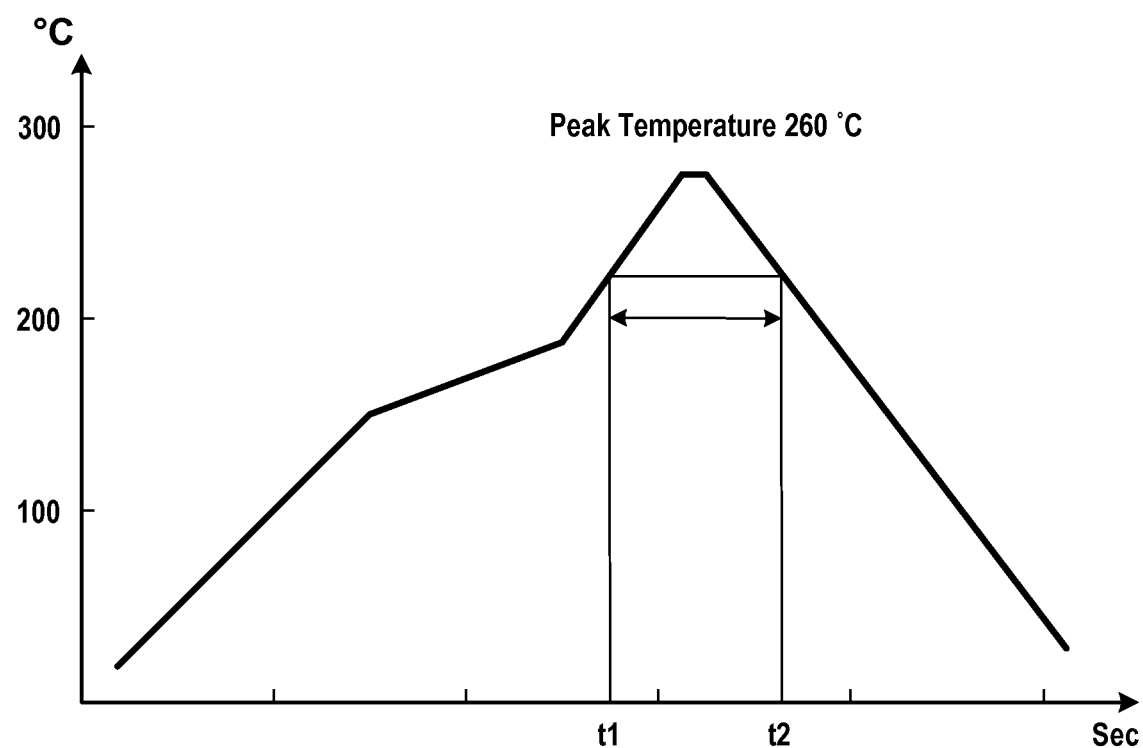
FIG. 1A illustrates an infra-red (IR) reflow temperature profile for an embedded storage device during the IR reflow process, in accordance with one embodiment of the present invention.

FIG. 1A illustrates an infra-red (IR) reflow temperature profile for an embedded storage device 100 during the IR reflow process, in accordance with one embodiment of the present invention. As shown, the temperature of the embedded storage device can reach to a peak temperature of 260° C. during the time frame between t1 and t2, The peak temperature is caused by the thermal shock occurred during the IR reflow process. A pre-defined threshold temperature for the embedded storage device 100 may be set based on the peak temperature of the IR reflow temperature profile, and the resistance state of the sensor device 150 inside the embedded storage device 100 may change from one resistance state to another resistance state when the temperature inside the embedded storage device 100 has reached the pre-defined threshold temperature. As discussed above, the threshold temperature may be defined within the range of about 250° C. to 300° C.

Figure 2:
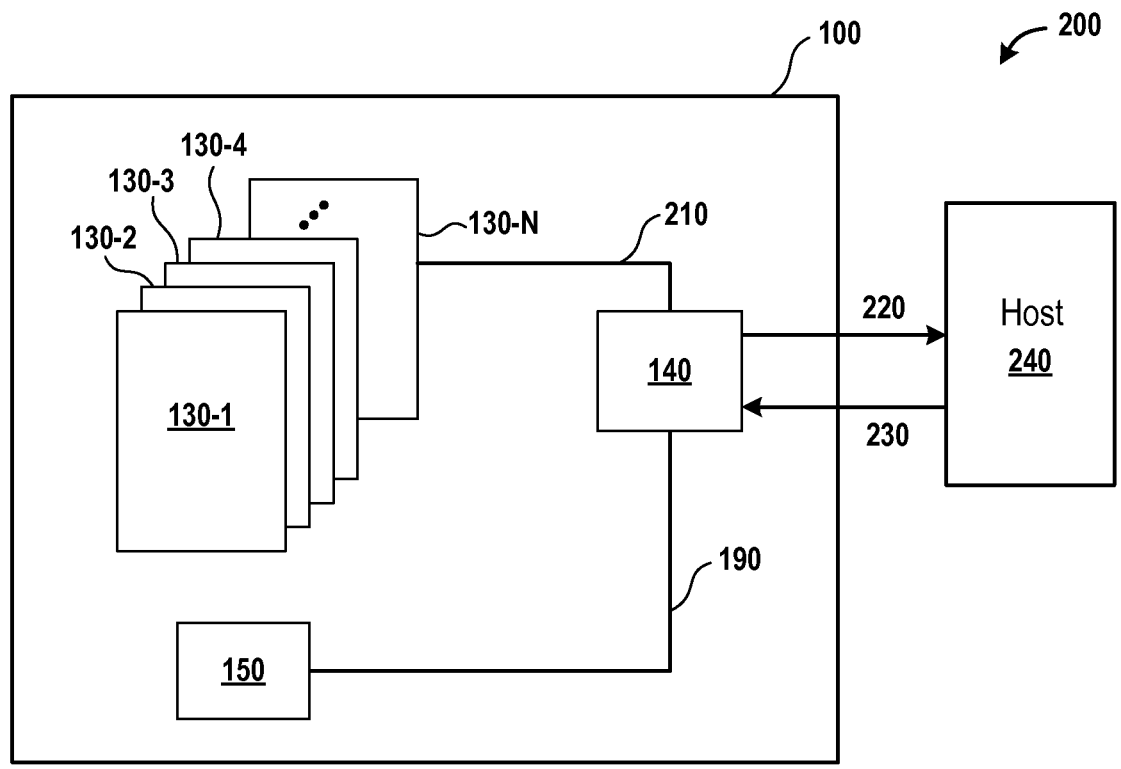
FIG. 2 illustrates a block diagram of a system for programming an embedded storage device, in accordance with one embodiment of the present invention.

FIG. 2 illustrates a block diagram of a system 200 for programming an embedded storage device 100, in accordance with one embodiment of the present invention. The system 200 includes an embedded storage device 100 and a host 240. Any number of well-known connections may be used to connect the host 240 with the embedded storage device 100. The host 240 may broadly define any device that needs to access an embedded storage device. For example, the host 240 may be a central controller that resides within the same semiconductor device with the embedded storage device 100. In another example, the host 240 may be a test controller when the embedded storage device is under test. In yet another example, the host 240 may be a computer, a phone, a tablet, or some other electronic device that needs to access memory.

In one embodiment, the controller 140 of the embedded storage device 100 respectively communicates with the memory chips 130_1 to 130_N via the control lines 210. The control lines 210 may include the bonding wire 180 and the bond wires 170, as shown in FIG. 1. The controller 140 of the embedded storage device 100 also communicates with the sensor device 150 via the bonding wire 190

In one embodiment, upon the request of the host 240, the controller 140 may generate an output 220 that indicates whether a reflow process, for example, an IR reflow process, has occurred to the embedded storage device 100. If the output 220 indicates that a reflow process has not occurred, the controller 140 of the embedded storage device 100 may receive a set up instruction from the host 240 via the input 230 such that the controller 140 may set the memory chips 130_1 to 130_N to a slow programming mode. If the output 220 indicates that a reflow process has occurred, the host 240 may send a set up instruction via the input 230 to the controller 140 such that the controller 140 may set the memory chips 130_1 to 130_N to a fast programming mode. In one embodiment, the memory chips 130_1 to 130_N are defaulted to the slow programming mode, and the programming speed defined by the slow programming mode is the default programming speed for the memory chips 130_1 to 130_N in the embedded storage device 100. In one embodiment, the output 220 of the controller 140 is based on the resistance change of the sensor device 150, which will be described in details in FIG. 3.

Figure 3A:
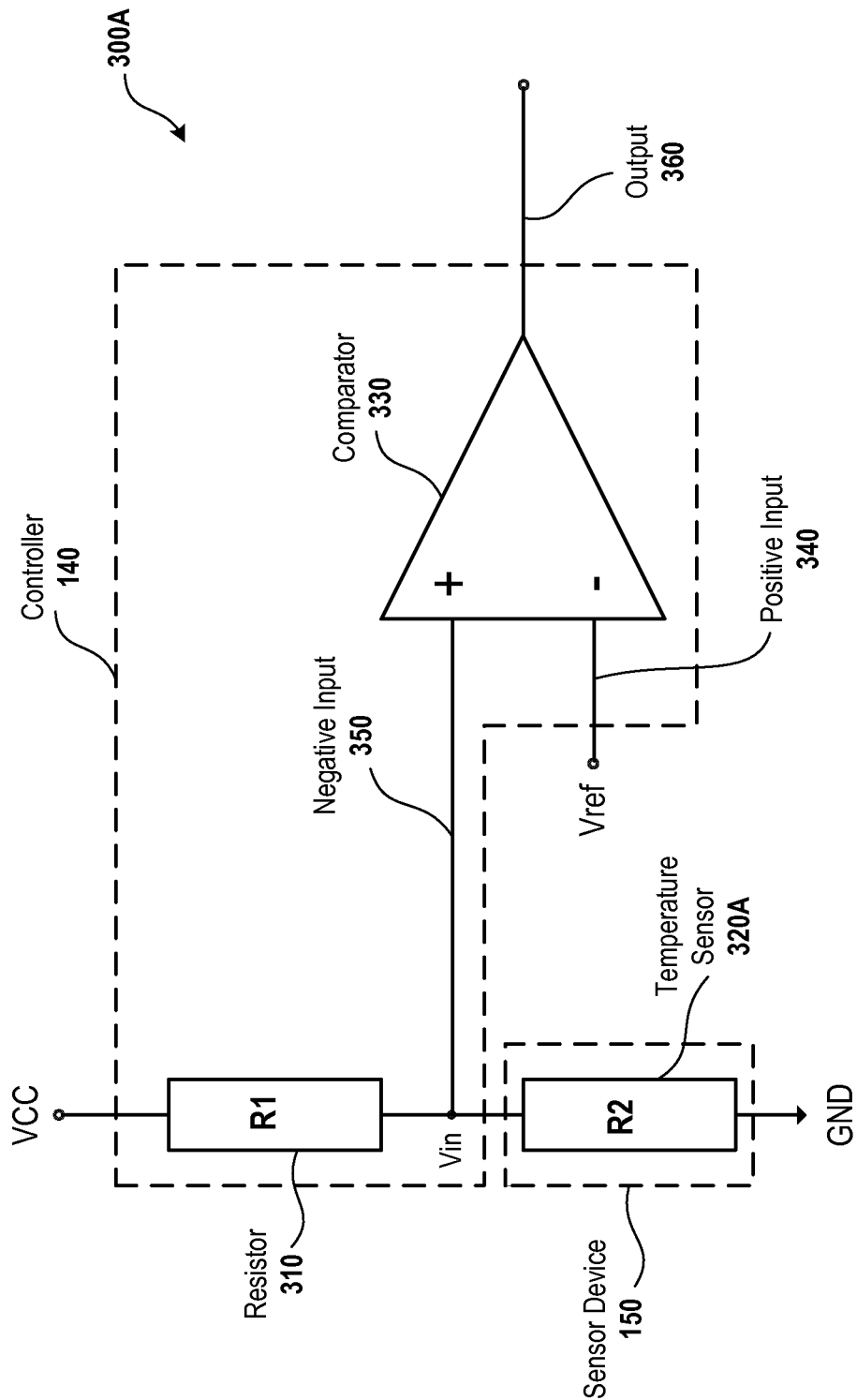
FIG. 3A illustrates a temperature sensing device, in accordance with one embodiment of the present invention.

FIG. 3A illustrates a temperature sensing device 300A, in accordance with one embodiment of the present invention. The temperature sensing device 300A includes a resistor 310, a temperature sensor 320A, and a comparator 330. The resistor 310 is a resistor having a first terminal and a second terminal. The first terminal of the resistor 310 is coupled to a voltage source Vcc and the second terminal of the resistor 310 is coupled the first terminal of temperature sensor 320A and the negative input 350 of the comparator 330. The positive input 340 of the comparator 330 is coupled to a reference voltage Vref. The second terminal of the temperature sensor 320A is grounded. The output 360 of the comparator 330 may indicate whether an IR reflow process has occurred to an embedded device at which the temperature sensing device 300A is located.

In one embodiment, the temperature sensing device 300A may be located inside an embedded storage device. In another embodiment, the temperature sensing device 300A may be embedded in any logic or memory chip for detecting reflow. In one embodiment, the resistor 310 and the comparator 330 may be located inside the controller 140 of the embedded storage device 100, and the temperature sensor 320A may be located inside the sensor device 150, as shown in FIG. 1 and FIG. 2.

In one embodiment, the temperature sensor 320A is made of phase change material the resistance of which changes from a first resistance state to a second resistance state if the temperature that surrounds the temperature sensor 320A reaches a threshold temperature. For example, the thermal shock caused by an IR reflow process for the embedded storage device 100 may elevate the temperature inside the embedded storage device 100 such that the temperature surrounding the temperature sensor 320A inside the sensor device 150 reaches the threshold temperature. In one embodiment, the threshold temperature is within the temperature ranges of the thermal shock caused by an IR reflow process.

In one embodiment, the temperature sensor 320A is a phase change memory (PCM) cell and the state of the phase change material inside the PCM cell has been pre-configured to the Reset state. The pre-configuration of the PCM cell may be performed in the embedded storage device production environment by applying a short thermal pulse to the PCM cell. In one embodiment, the short thermal pulse may have duration of about 1 mili-second. Accordingly, Vin (the voltage at the interconnection point of the resistor 310, the temperature sensor 320A, and the negative input 350 of the comparator 330) is high. When Vin is higher than the reference voltage Vref coupled to the positive input 340 of the comparator 330, the output 360 of the comparator 330 is false.

After an IR reflow process, the temperature surrounding the temperature sensor 320A elevates to the pre-defined threshold temperature, due to thermal shock having occurred during the IR reflow process. As a result, the state of the phase change material of the PCM cell changes from the Reset state to the Set state. Accordingly, the resistance state of the temperature sensor 320A changes from a first resistance state (e.g., high resistance state) to a second resistance (e.g., low resistance state). The reduced resistance of the temperature sensor 320A decreases Vin. When Vin is lower than Vref, the output 360 of the comparator 330 is true.

In one embodiment, the voltage source Vcc is about 3.3V, the reference voltage Vref is about $0.5 \times Vcc = 1.65V$, and the resistor 310 is about $5 \times 10^6$ ohms. Before an IR reflow process, the resistance of the temperature sensor 320A is about $5 \times 10^7$ ohms. If R1 represents the resistance of the resistor 310 and R2 represents the resistance of the temperature sensor 320A, $Vin = (R2 \times Vcc)/(R1+R2) = 5 \times 10^7 \times 3.3/(5 \times 10^6 + 5 \times 10^7) = 3.0V$. Since Vin (3.0V)>Vref (1.65V), the output 360 of the comparator 330 is false (e.g., 0V), indicating that an IR reflow process has not occurred. After an IR reflow process, the resistance of the temperature sensor 320 is about $5 \times 10^5$ ohms. Thus, $Vin = (R2 \times Vcc)/(R1+R2) = (5 \times 10^5 \times 3.3)/(5 \times 10^6 + 5 \times 10^5) = 0.3V$. Since Vin (0.3V)<Vref (1.65V), the output 360 of the comparator 330 is true (e.g., 3.3V), indicating that an IR reflow process has occurred.

Figure 3B:
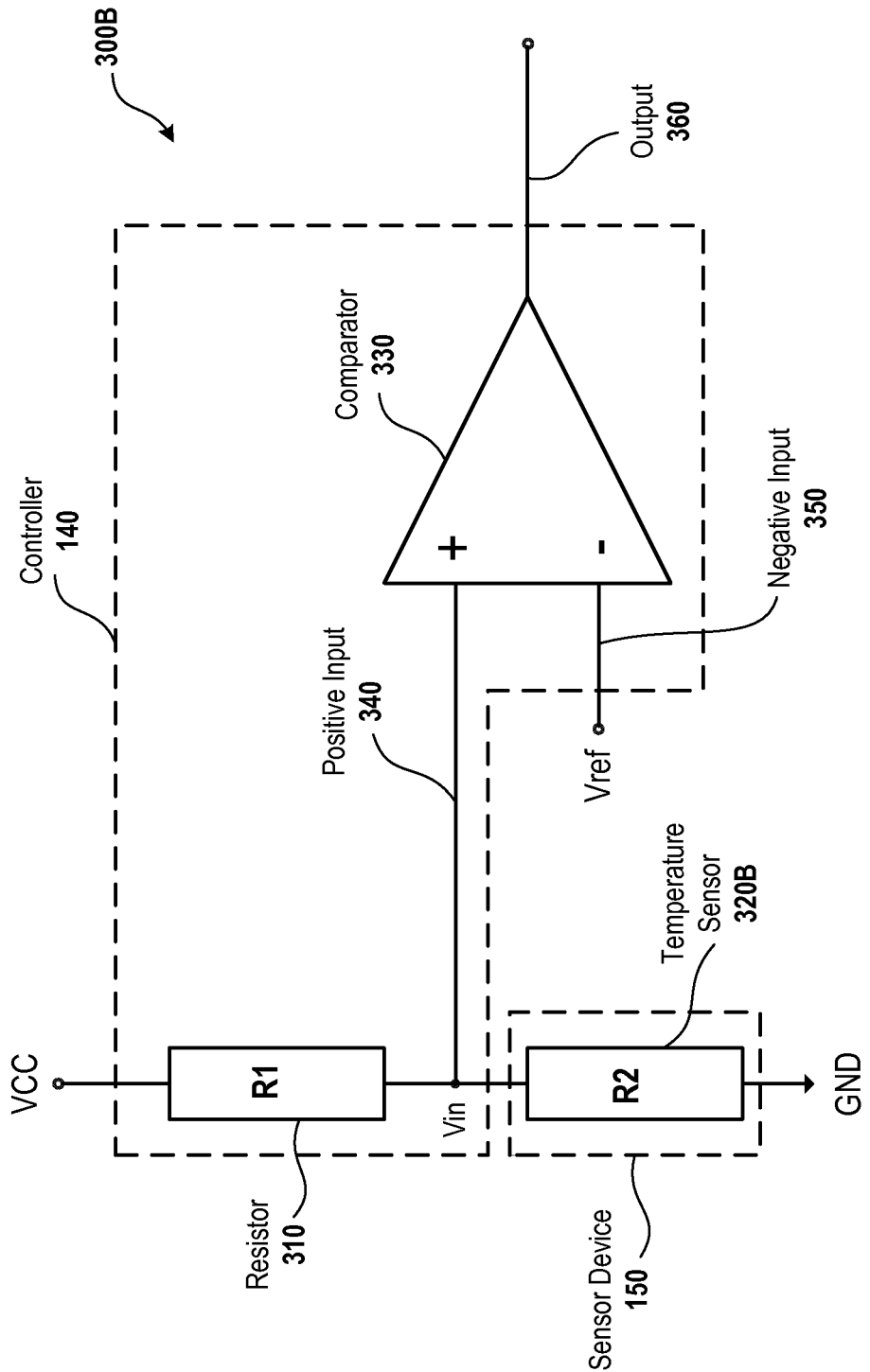
FIG. 3B illustrates a temperature sensing device, in accordance with one embodiment of the present invention.

FIG. 3B illustrates a temperature sensing device 300B, in accordance with one embodiment of the present invention. The temperature sensing device 300B includes a resistor 310, a temperature sensor 320B, and a comparator 330. The resistor 310 is a resistor having a first terminal and a second terminal. The first terminal of the resistor 310 is coupled to a voltage source Vcc and the second terminal of the resistor 310 is coupled the first terminal of temperature sensor 320B and the positive input 340 of the comparator 330. The negative input 350 of the comparator 330 is coupled to a reference voltage Vref. The second terminal of the temperature sensor 320B is grounded. The output 360 of the comparator 330 may indicate whether an IR reflow process has occurred to an embedded device at which the temperature sensing device 300B is located.

In one embodiment, the temperature sensing device 300B may be located inside an embedded storage device. In another embodiment, the temperature sensing device 300B may be embedded in any logic or memory chip for detecting reflow. In one embodiment, the resistor 310 and the comparator 330 may be located inside the controller 140 of the embedded storage device 100, and the temperature sensor 320B may be located inside the sensor device 150.

In one embodiment, the temperature sensor 320B is a metal device made of Tin and Lead Alloy. The resistance of the metal device (or the temperature sensor 320B) changes from one resistance state to another resistance state if the temperature that surrounds the temperature sensor 320B reaches a threshold temperature. For example, the thermal shock caused by an IR reflow process for the embedded storage device 100 may elevate the temperature inside the embedded storage device 100 such that the temperature surrounding the temperature sensor 320B inside the sensor device 150 reaches the threshold temperature. In one embodiment, the threshold temperature is within the temperature ranges of the thermal shock caused by an IR reflow process. As discussed above, in one embodiment, the threshold temperature is in the range of about 250° C. to 300° C.

In one embodiment, the temperature sensor 320B has a low resistance state before an IR reflow process. Accordingly, Vin (the voltage at the interconnection point of the resistor 310, the temperature sensor 320B, and the positive input 340 of the comparator 330) is low. When Vin is lower than the reference voltage Vref coupled to the negative input 350 of the comparator 330, the output 360 of the comparator 330 is false.

After an IR reflow process, the temperature surrounding the temperature sensor 320B elevates to the pre-defined threshold temperature, due to thermal shock having occurred during the IR reflow process. As a result, the resistance of the temperature sensor 320B has changed from the low resistance state to a high resistance state. The increased resistance of the temperature sensor 320B causes Vin to increase. When Vin is higher than Vref, the output 360 of the comparator 330 is true. FIG. 6A and FIG. 6B will describe the resistance change of the temperature sensor 320B in details.

In one embodiment, the output 360 of the comparator 330, as shown in both FIG. 3A and FIG. 3B, is illustrated by the output 220 of the controller 140 in FIG. 2. A host, for example, the host 240 in FIG. 2, may measure the output 360 of the comparator 330 after each power up or when the embedded storage device 100 is initiated to determine whether an IR reflow process has occurred to the embedded storage device 100. If the output 360 is false, which means the IR reflow process has not yet occurred to the embedded storage device 100, the host 240 may send an instruction via the input 230 to the controller 140 such that the controller 140 may set the memory chips 130_1 to 130_N to a slow programming mode. Alternatively, if the memory chips 130_1 to 130_N have been preconfigured to have the slow programming speed as the default programming speed, the host 240 will not send any instructions to change the programming speed for those memory chips when the output 360 is detected to be false. If the output 360 is true, which means the IR reflow process has occurred to the embedded storage device 100, the host 240 may send an instruction via the input 230 to the controller 140 such that the controller 140 may set the memory chips 130_1 to 130_N to a fast programming mode. The slow programming speed set for the memory chips 130_1 to 130_N before an IR reflow process will provide good resiliency to any preloaded data in these memory chips so that the preloaded data can sustain the thermal shock occurred during the IR reflow process. The fast programming speed set for the memory chips 130_1 to 130_N after the IR reflow process will improve the memory chip performance without any risks to the preloaded data in the memory chips.

Figure 4A:
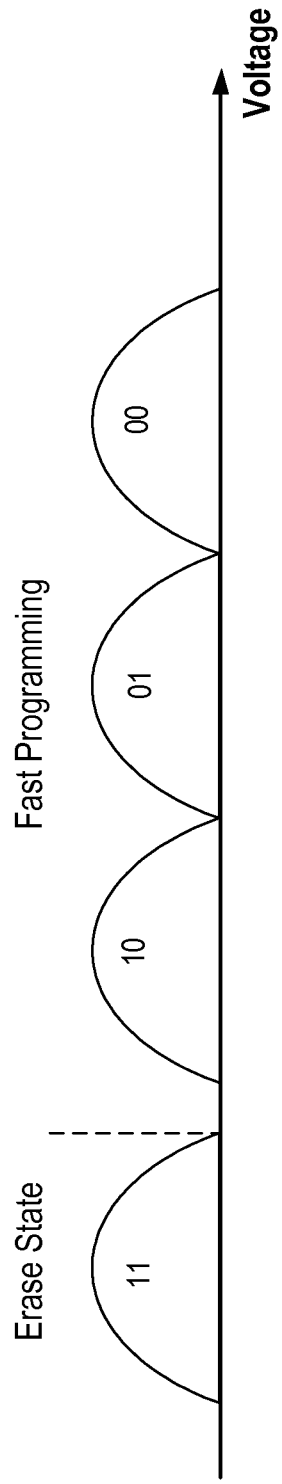
FIGS. 4A and 4B illustrate voltage distribution diagrams of a NAND memory cell programmed in a fast programming mode and in a slow programming mode, respectively, in accordance with one embodiment of the present invention.
Figure 4B:
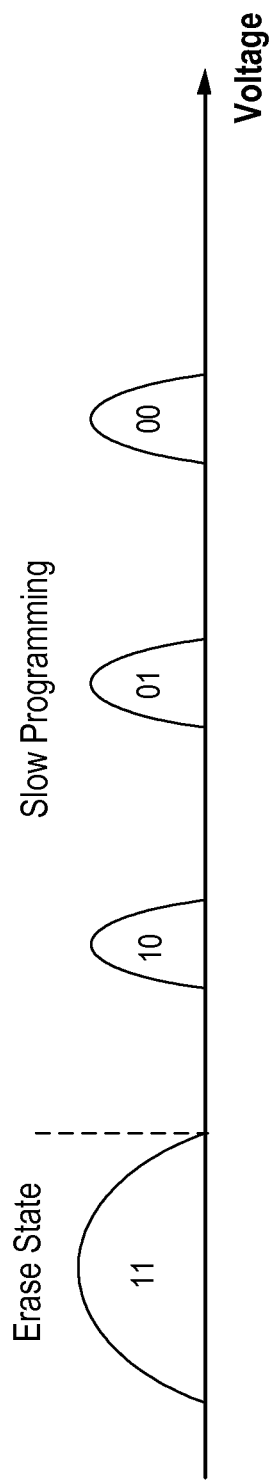

FIGS. 4A and 4B illustrate voltage distribution diagrams of a NAND memory cell programmed in a fast programming mode and in a slow programming mode, respectively, in accordance with one embodiment of the present invention. In this embodiment, the NAND memory cell is a multi-level cell (MLC) capable of storing 2 bits per cell.

FIG. 4A shows the voltage distributions of a NAND memory cell programmed in the fast programming mode. FIG. 4B shows the voltage distributions of a NANA memory cell programmed in the slow programming mode. As shown, the voltage distributions of the NAND memory cell programmed in the fast programming mode are wide spread along the voltage axis, while the NAND memory cell programmed in the slow programming mode yields tighter or narrower voltage distributions along the voltage axis. In one embodiment, the slow programming speed of a NAND memory cell is the default programming speed of the NAND memory cell.

The narrow voltage distributions of a NAND memory cell are more resilient to an IR reflow process than the wide distributions of the NAND memory cell, because the floating gates of the NAND memory cell may be fully charged in the slow programming mode such that the data stored in the NAND memory cell can have better survive margin during the thermal shock caused by a reflow process. In one embodiment, the fast programming speed for a NAND memory cell is about 10 MB/sec. In one embodiment, the slow programming speed for a NAND memory cell is about 5 MB/s.

FIGS. 5A and 5B illustrate resistance changes of a phase change memory (PCM) cell 500 before and after an IR reflow process, in accordance with one embodiment of the present invention.

In one embodiment, the phase change material inside the PCM cell 500 is Chalcogenide having two states: Set (low resistance crystalline) state and Reset (high resistance amorphous) state. When the PCM cell 500 is exposed to a relatively low temperature for a long time, the state of the PCM cell 500 is at the Set state. When the PCM cell 500 is exposed to a relatively high temperature for a short period of time, the state of the PCM cell 500 will change from the Set state to the Reset state. The temperature ranges for the Set state of the PCM cell 500 are about 180° C. to 269° C., while the temperature ranges for the Reset state are about 610° C. to 720° C. In one embodiment, a short thermal pulse may be applied to the PCM cell 500 so as to pre-configure the PCM cell 500 from the Set state to the default Reset state. In one embodiment, the short thermal pulse has duration of about 1 mili-second with a temperature of above 600° C.

FIG. 5A shows the Reset (Amorphous) state of the PCM cell 500 before an IR reflow process. As shown, the PCM cell 500 includes a top electrode 510, a polycrystalline Chalcogenide layer 520, a resistor 530, and a bottom electrode 540. An active phase change region 550 is formed inside the polycrystalline Chalcogenide layer 520. At the Reset state, the resistance of the PCM cell 500 is high due to the formation of the active phase change region 550.

FIG. 5B shows the Set (Crystalline) state of the PCM cell 500 after the IR reflow process. Because the active phase change region 550 does not exist in the polycrystalline Chalcogenide layer 520 at the Set state, the resistance of the PCM cell 500 is low.

During an IR reflow process; the heat produced from the thermal shock causes an active phase change region 550 to be formed inside the polycrystalline Chalcogenide layer 520 at the intersection between the polycrystalline Chalcogenide layer 520 and the resistor 530. At the Reset state, the resistance of the PCM cell 500 is high due to the active phase change region 550.

In one embodiment, the PCM cell 500 may be used as the temperature sensor 320 in the temperature sensing device 300 and is pre-programmed to the Set state. The top electrode 510 of the PCM cell 500 may be coupled to the positive input 340 of the comparator 330 and the second terminal of the resistor 310, and the bottom electrode 540 of the PCM cell 500 may be grounded.

FIGS. 6A and 6B illustrate resistance changes of a metal device 600 before and after an IR reflow process, in accordance with one embodiment of the present invention. The metal device 600 includes a metal terminal 610, a metal terminal 620, and a metal wire 630. The two metal terminals 610 and 620 are connected by the metal wire 630. The two metal terminals 610 and 620 are made of a first metal material with a very high melting temperature (higher the highest temperature occurred during an IR reflow process) such that the two metal terminals 610 and 620 do not get deformed during the IR reflow process. Examples of the first metal material are 24 K pure Gold with a melting temperature of 1063° C./1945° F. or Aluminum with a melting temperature of 660° C./1220° F. The metal wire 630 is made of a second metal material with a lower melting temperature than the one of the first metal material, such that the metal wire 630 will melt while being exposed to the IR reflow process but will be intact under normal operating temperatures (e.g., from −40° C. to 85° C.). For example, the second metal material may be an alloy of 50% tin and 50% lead_with a melting temperature of 185-215° C. (365-419° F.) In one embodiment, the melting temperature of the metal wire 630 is within the temperature ranges of the thermal shock caused by an IR reflow process.

In one embodiment, the metal device 600 may be used as the temperature sensor 320 in the temperature sensing device 300 as shown in FIG. 3. For example, the metal terminal 610 of the metal device 600 may be coupled to the positive input 340 of the comparator 330 and the second terminal of the resistor 310 and the metal terminal 620 may be grounded.

FIG. 6A shows the metal device 600 before an IR reflow process. Being intact under normal operating temperatures, the metal wire 630 connects the two metal terminals 610 and 620. As such, the metal device 600 shows a low resistance.

As shown in FIG. 6B, after an IR reflow process, the metal wire 630 is deformed and broken into two sections 640 and 650, due to the high temperature caused by the thermal shock during the IR reflow process. In one embodiment, after the metal wire 630 breaks up, the surface tension may change the shape of the section 640 into to a ball. Because the metal terminal 610 is disconnected with the metal terminal 620, and metal device 600 shows a very high resistance.

Figure 7:
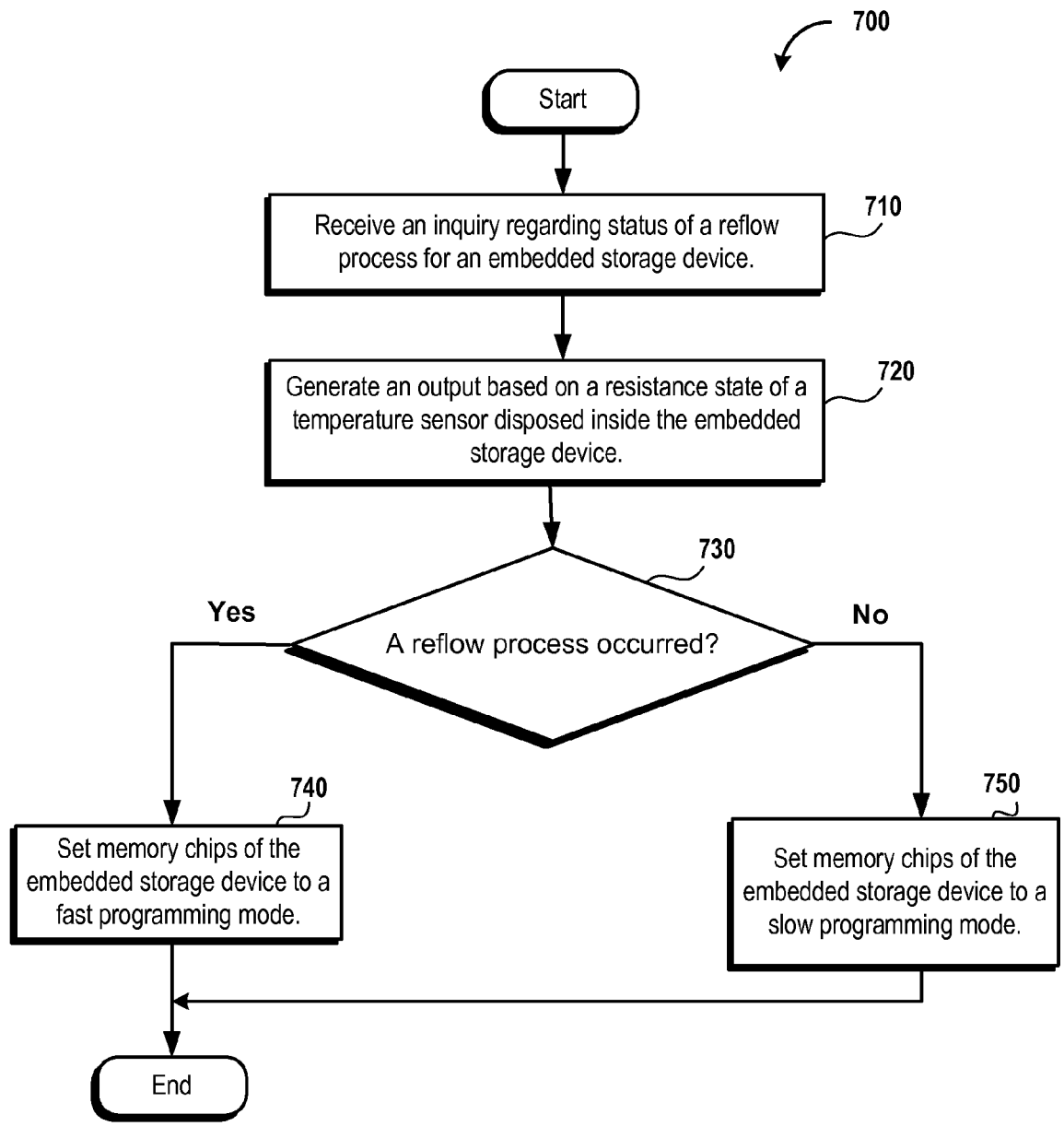
FIG. 7 illustrates a flow diagram of an exemplary method for detecting whether a reflow process has occurred to an embedded storage device, in accordance with one embodiment of the present invention.

FIG. 7 illustrates a flow diagram of an exemplary method 700 for detecting whether a reflow process has occurred to an embedded storage device 100, in accordance with one embodiment of the present invention. In one embodiment, the illustrated exemplary method 700 is described in relation to the system 200 and the temperature sensing device 300 as shown in FIGS. 2 and 3, respectively.

In operation 710, the embedded storage device 100 receives an inquiry regarding the status of a reflow process for the embedded storage device 100. The status of a reflow process may indicate whether a reflow process has occurred to the embedded storage device 100. In one embodiment, the inquiry is sent by the host 240 during every power up, as shown in FIG. 2. In another embodiment, the inquiry is sent by the host 240 whenever the embedded storage device is initiated. In yet another embodiment, the inquiry may be sent by the host 240 upon a request from a user.

In operation 720, the embedded storage device 100 generates an output, indicating whether a reflow process has occurred to the embedded storage device 100. For example, the controller 140 of the embedded storage device 100 may generates an output 220 to the host 240 in response to the inquiry sent from the host 240. As discussed above, the output 220 of the controller 140 may be the output 360 of the comparator 330 of the temperature sensing device 300A or the temperature sensing device 300B as shown in FIGS. 3A and 3B, and the output 360 is generated based on the resistance state of the temperature sensor 320A disposed inside the temperature sensing device 300A or based on the resistance state of the temperature sensor 320B disposed inside the temperature sensing device 300B.

In operation 730, a determination is made as to whether a reflow process has occurred to the embedded storage device 100 based on the output generated by the embedded storage device 100. In one embodiment, the determination may be made by the host 240 coupled to the embedded storage device 100.

In operation 740, if a reflow process has occurred to the embedded storage device 100, the memory chips, for example, the memory chips 130_1 to 130_N inside the embedded storage device 100, are set to be programmed in a fast programming mode. In one embodiment, the host 240 sends the fast programming instructions to the controller 140 that in turn sets the programming speeds for the memory chips 130_1 to 130_N.

In operation 750, if a reflow process has not occurred to the embedded storage device 100, the memory chips, for example, the memory chips 130_1 to 130_N inside the embedded storage device 100, are set to be programmed in a slow programming mode. In one embodiment, the host 240 sends the slow programming instructions to the controller 140 that in turn sets the programming speeds for the memory chips 130_1 to 130_N. Alternatively, if the memory chips 130_1 to 130_N have the slow programming speed as the default speed, the host 240 may not send any instructions to the controller 140 when the reflow process has not occurred to the embedded storage device 100.

The embodiment or parts of the embodiment described herein can be defined as computer readable code on a computer readable medium. The computer readable medium mentioned herein is any data storage device that can store data which can thereafter be read by a computer system. Examples of the computer readable medium include hard drives, network attached storage (NAS), read-only memory, random-access memory, CD-ROMs, CD-Rs, CD-RWs, magnetic tapes, and other optical and non-optical data storage devices. The computer readable medium can also be distributed over a network of coupled computer systems so that the computer readable code is stored and executed in a distributed fashion.

Any of the operations described herein that form part of the invention are useful machine operations. The invention also relates to a device or an apparatus for performing these operations. The apparatus may be specially constructed for the required purpose, such as a special purpose computer. When defined as a special purpose computer, the computer can also perform other processing, program execution or routines that are not part of the special purpose, while still being capable of operating for the special purpose. Alternatively, the operations may be processed by a general purpose computer selectively activated or configured by one or more computer programs stored in the computer memory, cache, or obtained over a network. When data is obtained over a network the data may be processed by other computers on the network, e.g., a cloud of computing resources.

The embodiments of the present invention can also be defined as a machine that transforms data from one state to another state. The data may represent an article, that can be represented as an electronic signal and electronically manipulate data. The transformed data can, in some cases, be visually depicted on a display, representing the physical object that results from the transformation of data. The transformed data can be saved to storage generally, or in particular formats that enable the construction or depiction of a physical and tangible object. In some embodiments, the manipulation can be performed by a processor. In such an example, the processor thus transforms the data from one thing to another. Still further, the methods can be processed by one or more machines or processors that can be connected over a network. Each machine can transform data from one state or thing to another, and can also process data, save data to storage, transmit data over a network, display the result, or communicate the result to another machine.

While this invention has been described in terms of several embodiments, it will be appreciated that those skilled in the art upon reading the preceding specifications and studying the drawings will realize various alterations, additions, permutations and equivalents thereof. Therefore, it is intended that the present invention includes all such alterations, additions, permutations, and equivalents as fall within the true spirit and scope of the invention.

What is claimed is:

1. A temperature sensing device, comprising:
    a resistor having a first terminal coupled to a voltage source;
    a temperature sensor having a first terminal coupled to a second terminal of the resistor and a second terminal of the temperature sensor being grounded, wherein resistance of the temperature sensor changes from a first resistance state to a second resistance state after temperature surrounding the temperature sensing device reaches a threshold temperature;
    a comparator having a first input and a second input, wherein the first input of the comparator is coupled to the second terminal of the resistor and the first terminal of the temperature sensor, and the second input of the comparator is coupled to a reference voltage,
    wherein the comparator generates an output based on resistance changes of the temperature sensor, indicating temperature changes for the temperature sensing device.

2. The temperature sensing device of claim 1, wherein the temperature sensor is a phase change memory (PCM) cell.

3. The temperature sensing device of claim 2, wherein the first resistance state of the temperature sensor is a high resistance state and the second resistance state of the temperature sensor is a low resistance state.

4. The temperature sensing device of claim 2, wherein the first input of the comparator is a negative input and the second input of the comparator is a positive input.

5. The temperature sensing device of claim 1, wherein the temperature sensor is a metal device that includes,
    a first metal terminal,
    a second metal terminal, and
    a metal wire, wherein the first metal terminal is coupled to the second metal terminal through the metal wire, the first and second metal terminals are made of a first metal material having a high melting temperature that is higher than highest temperature of a thermal shock caused by a reflow process, and the metal wire is made of a second metal material having a low melting temperature that is within temperature ranges of the thermal shock caused by the reflow process.

6. The temperature sensing device of claim 5, wherein the first resistance state of the temperature sensor is a low resistance state and the second resistance state of the temperature sensor is a high resistance state.

7. The temperature sensing device of claim 5, wherein the first input of the comparator is a positive input and the second input of the comparator is a negative input.

8. The temperature sensing device of claim 1, wherein the output of the comparator is false when the temperature sensor is in the first resistance state and is true when the temperature sensor is in the second resistance state.

9. The temperature sensing device of claim 1, wherein the threshold temperature is within temperature ranges of a thermal shock caused by a reflow process.

10. The temperature sensing device of claim 1, wherein the temperature sensing device is located inside an embedded storage device.

11. A system for detecting occurrence of a reflow process, comprising:
    a host;
    an embedded storage device including,
        a plurality of memory chips,
        a controller coupled to the plurality of memory chips, the controller
        including a comparator, and
        a temperature sensor coupled to the comparator, resistance of the temperature sensor changing from a first resistance state to a second resistance state during the reflow process for the embedded storage device, the second resistance state being an input to the comparator to generate an output indicative that the reflow process occurred,
    wherein the host is coupled to the embedded storage device through the controller.

12. The system of claim 11, wherein the host is configured to set the memory chips inside the embedded storage device in a slow programming mode if the output of the controller indicates that the reflow process has not occurred to the embedded storage device, or to set the memory chips inside the embedded storage device in a fast programming mode if the output the controller indicates that the reflow process has occurred to the embedded storage device.

13. The system of claim 11, wherein the embedded storage device is configured to set the memory chips in a slow programming mode if the output of the controller indicates that the reflow process has not occurred to the embedded storage device, or to set the memory chips in a fast programming mode if the output the controller indicates that the reflow process has occurred to the embedded storage device.

14. The system of claim 11, wherein the output of the controller of the embedded storage device is obtained generated upon an inquiry sent from the host.

15. The system of claim 11, wherein the temperature sensor is a phase change memory (PCM) cell.

16. The system of claim 11, wherein the temperature sensor is a metal device that includes,
    a first metal terminal,
    a second metal terminal, and
    a metal wire, wherein the first metal terminal is coupled to the second metal terminal through the metal wire, the first and second metal terminals are made of a first metal material having a high melting temperature that is higher than highest temperature of a thermal shock caused by the reflow process, and the metal wire is made of a second metal material having a low melting temperature that is within temperature ranges of the thermal shock caused by the reflow process.

17. A method of programming an embedded storage device, comprising:
    generating an output by the embedded storage device based on a resistance state of a temperature sensor disposed inside the embedded storage device, the output being generated by a controller that includes a comparator, the comparator is coupled to a temperature sensor that changes from a first state to a second state after the embedded storage device experiences thermal shock;
    determining, by the comparator that the temperature sensor changed to the second state which is indicative that a reflow process has occurred to the embedded storage device based on the generated output by the controller; and setting, by the controller, the memory chips of the embedded storage device to a fast programming mode after the reflow process has occurred to the embedded storage device.

18. The method of claim 17, further comprising:
setting the memory chips of the embedded storage device to a slow programming mode while the reflow process has not occurred to the embedded storage device.

19. The method of claim 17, further comprising:
preconfiguring the memory chips of the embedded storage device to a slow programming mode.

20. The method of claim 17, further comprising:
sending an inquiry to the controller regarding reflow status of the embedded storage device when the embedded storage device is initiated.

\* \* \* \* \*